US007996997B2

(12) United States Patent
Warntjes et al.

(10) Patent No.: US 7,996,997 B2
(45) Date of Patent: Aug. 16, 2011

(54) SPECTACLE MEASURING TOOL

(75) Inventors: Hans Warntjes, Tokyo (JP); Takashi Hatanaka, Tokyo (JP)

(73) Assignee: Hoya Corporation, Toyko (JP)

( * ) Notice: Subject to any disclaimer, the term of this patent is extended or adjusted under 35 U.S.C. 154(b) by 0 days.

(21) Appl. No.: 12/809,018

(22) PCT Filed: Dec. 22, 2008

(86) PCT No.: PCT/JP2008/073299
§ 371 (c)(1),
(2), (4) Date: Nov. 17, 2010

(87) PCT Pub. No.: WO2009/081898
PCT Pub. Date: Jul. 2, 2009

(65) Prior Publication Data
US 2011/0047807 A1    Mar. 3, 2011

(30) Foreign Application Priority Data

Dec. 20, 2007 (JP) .................................. 2007-328755

(51) Int. Cl.
*G01B 1/00* (2006.01)
*A61B 3/10* (2006.01)
(52) U.S. Cl. ............................. 33/200; 33/28; 351/204
(58) Field of Classification Search .............. 33/28, 200, 33/507; 351/204, 213, 233
See application file for complete search history.

(56) References Cited

U.S. PATENT DOCUMENTS

| 4,055,900 A * | 11/1977 | Grolman et al. ............. 351/204 |
| 4,190,331 A * | 2/1980 | Padula net al. ............. 351/204 |
| 2010/0064533 A1* | 3/2010 | Miyashita ..................... 33/200 |

FOREIGN PATENT DOCUMENTS

| DE | 200 15 424 U1 | 12/2000 |
| EP | 0 567 817 A1 | 11/1993 |
| EP | 2233066 A1 * | 9/2010 |
| JP | S58-203415 A | 11/1983 |
| JP | H08-098810 A | 4/1996 |
| JP | 2001-161645 A | 6/2001 |
| JP | 2001-340296 A | 12/2001 |
| JP | 2003-339640 A | 12/2003 |
| JP | 2007-522496 A | 8/2007 |
| JP | 2007-289683 A | 11/2007 |

* cited by examiner

*Primary Examiner* — Yaritza Guadalupe-McCall
(74) *Attorney, Agent, or Firm* — Blakely, Sokoloff, Taylor & Zafman

(57) ABSTRACT

A spectacle measuring tool (1) includes a front plate (2) attached to a spectacle frame, and a pair of left and right side plates (40A, 40B) formed on the two, left and right edges of the front plate (2) to extend backward. The front plate (2) includes an interpupillary distance measuring portion (A) and a fitting point height measuring portion (B), and is attached to the spectacle frame such that a height adjusting device (30) can adjust its height. The side plates (40A, 40B) include a pair of left and right pressing/adjusting devices (60) which adjust the side plates (40A, 40B) to be parallel to the temples of the spectacle frame. The pressing/adjusting devices (60) press against the face side portions of a subject using threaded rods (62).

5 Claims, 6 Drawing Sheets

SPECTACLE MEASURING TOOL

This is a non-provisional application claiming the benefit of International application number PCT/JP2008/073299 filed Dec. 22, 2008.

TECHNICAL FIELD

The present invention relates to a spectacle measuring tool which can measure, e.g., the interpupillary distance and fitting point heights of a subject.

BACKGROUND ART

When round lenses (uncut lenses) are edged so as to fit with the shapes of the left and right rims of a spectacle frame, shifts between the fitting points of the left and right eyes of the spectacle wearer (that are the pupil positions of the left and right eyes of the wearer in a spectacle frame when he or she wears the spectacle frame, and will also be referred to as IPs hereinafter) and the optical centers of the left and right lenses, if any, greatly influence the comfort upon wearing the spectacle. In this respect, it is necessary to precisely measure the interpupillary distance (to be also referred to as PD hereinafter) between the left and right pupils or the distances (to be also referred to as monocular PDs hereinafter) from the center of the bridge of the nose of the wearer to the left and right pupils to determine the optical center distance between the left and right lenses, and edge the respective lenses so that the optical centers of the respective lenses coincide with the IPs of the left and right eyes. To meet this requirement, a measuring tool disclosed in, for example, Japanese Patent Laid-Open No. 8-98810 measures PD or monocular PDs.

A fitting point measuring tool described in Japanese Patent Laid-Open No. 8-98810 easily, precisely measures the positions, in the horizontal direction and height direction, of the pupils of the left and right eyes of the subject. This fitting point measuring tool includes a base member, a clip-shaped attachment portion, and left and right movable members. The base member is placed on the front portion of a spectacle frame parallel to it. The attachment portion is used to attach the base member to the spectacle frame. The movable members are attached to the base member to be movable in its longitudinal direction (horizontal direction), and are individually aligned with the pupils of the left and right eyes of the subject. The base member is marked with horizontal scales for measuring the positions of the pupils in the horizontal direction, and the movable members are marked with vertical scales for measuring the positions of the pupils in the vertical direction.

DISCLOSURE OF INVENTION

Problem to be Solved by the Invention

Unfortunately, because the fitting point measuring tool described in Japanese Patent Laid-Open No. 8-98810 mentioned above adopts a structure in which a pair of bifurcated clamping members clamp the central portion of the spectacle frame at two points, it is difficult to precisely adjust the height of this tool relative to the spectacle frame, so the this tool is likely to tilt or shift in the vertical and horizontal directions. Another problem in handling is that the heights of the left and right movable members need to be individually adjusted relative to the base member every time such a shift or tilt occurs.

The present invention has been made to overcome the above-mentioned conventional problems, and has as its object to provide a spectacle measuring tool which has a structure simple enough to easily handle it, can be attached to spectacle frames with various shapes in a stable state, and can precisely measure the interpupillary distance between the left and right pupils and the fitting point heights.

Means of Solution to the Problem

In order to achieve the above-mentioned object, the present invention provides a spectacle measuring tool comprising a transparent, front plate which comprises a first measuring portion which measures an interpupillary distance and a second measuring portion which measures fitting point heights, and is attached to a front portion of a spectacle frame, a height adjusting device which adjusts a height of the front plate relative to the spectacle frame, a pair of left and right side plates placed on two, left and right edges of the front plate to extend backward, and a pair of left and right pressing/adjusting devices which are attached to the respective side plates, press against face side portions of a subject, and adjust the side plates to be parallel to temples of the spectacle frame.

Effects of the Invention

According to the present invention, since the spectacle measuring tool includes the height adjusting device, it can easily, precisely adjust the height of the front plate relative to the spectacle frame. Also, since this tool includes the pressing/adjusting device, it can press the respective side plates against the vicinities of the temples of the subject and adjust the temple portions of the spectacle frame and the side plates to be parallel to each other.

BEST MODE FOR CARRYING OUT THE INVENTION

Figure 3:
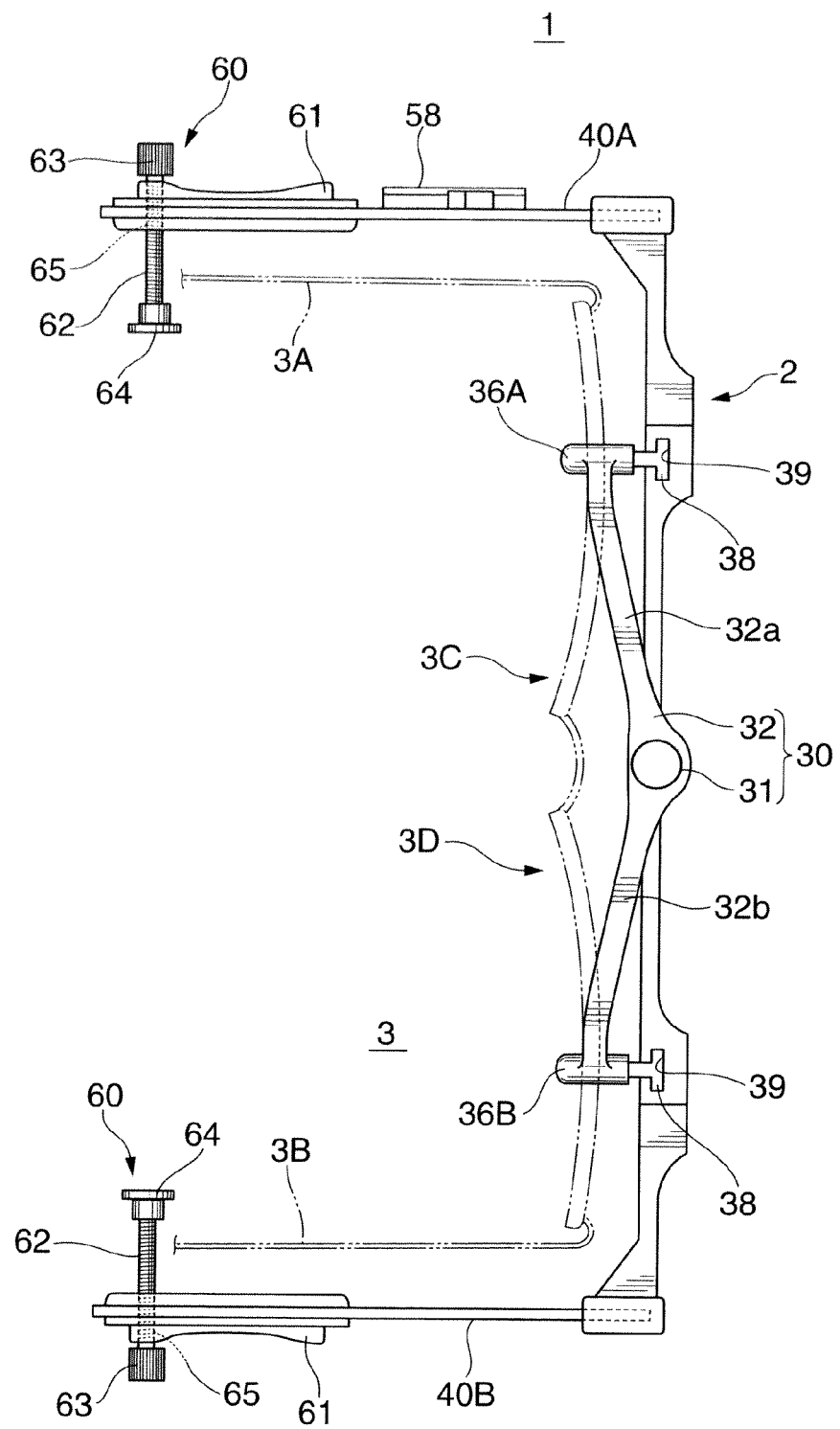
FIG. 3 is a plan view of the spectacle measuring tool.

Referring to FIGS. 1 to 7, a spectacle measuring tool 1 includes a front plate 2 attached to the front portion of a spectacle frame 3 parallel to it (FIG. 3).

Figure 1:
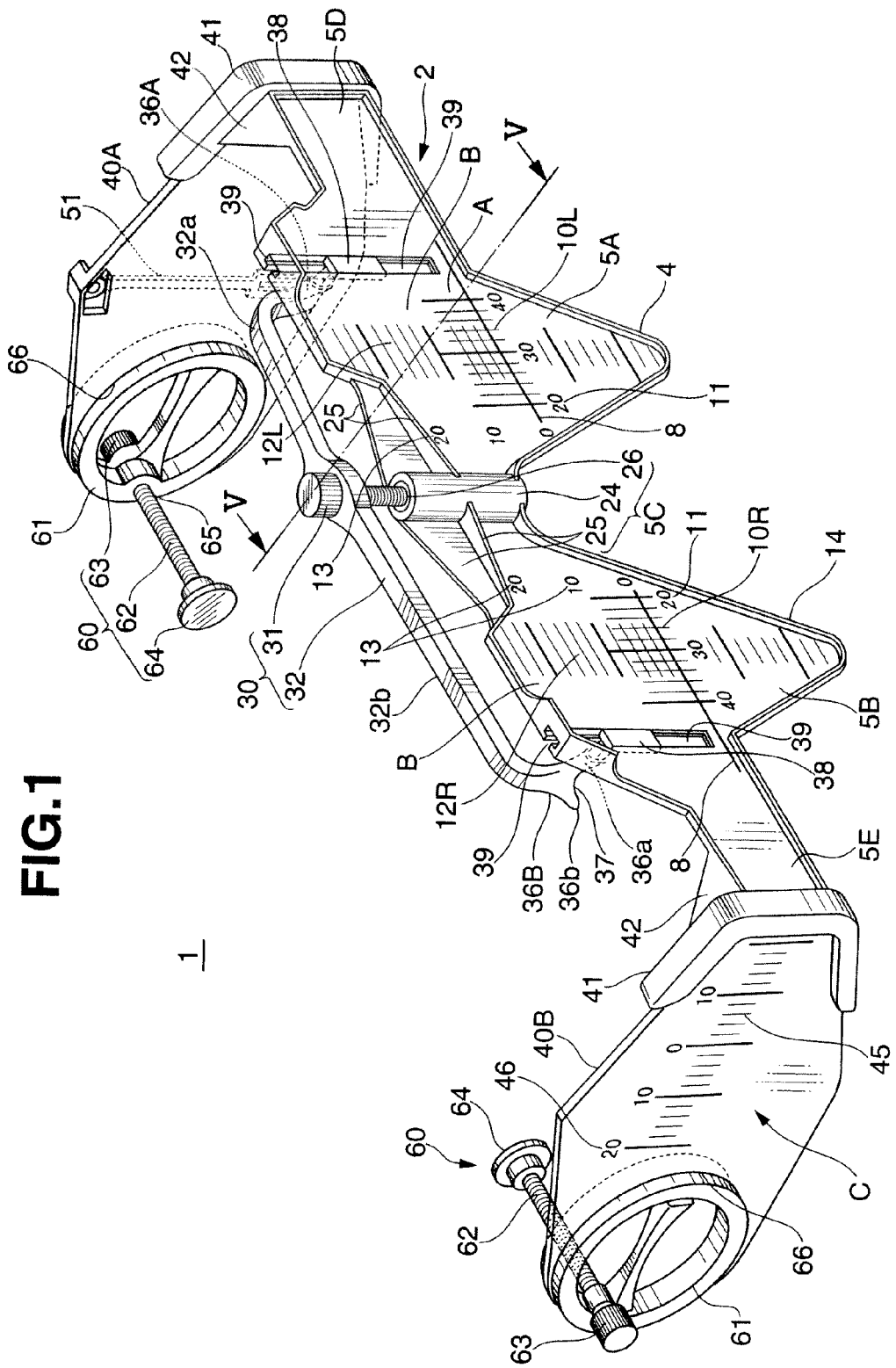
FIG. 1 is a perspective view showing the outer appearance of a spectacle measuring tool according to one embodiment of the present invention.
Figure 2:
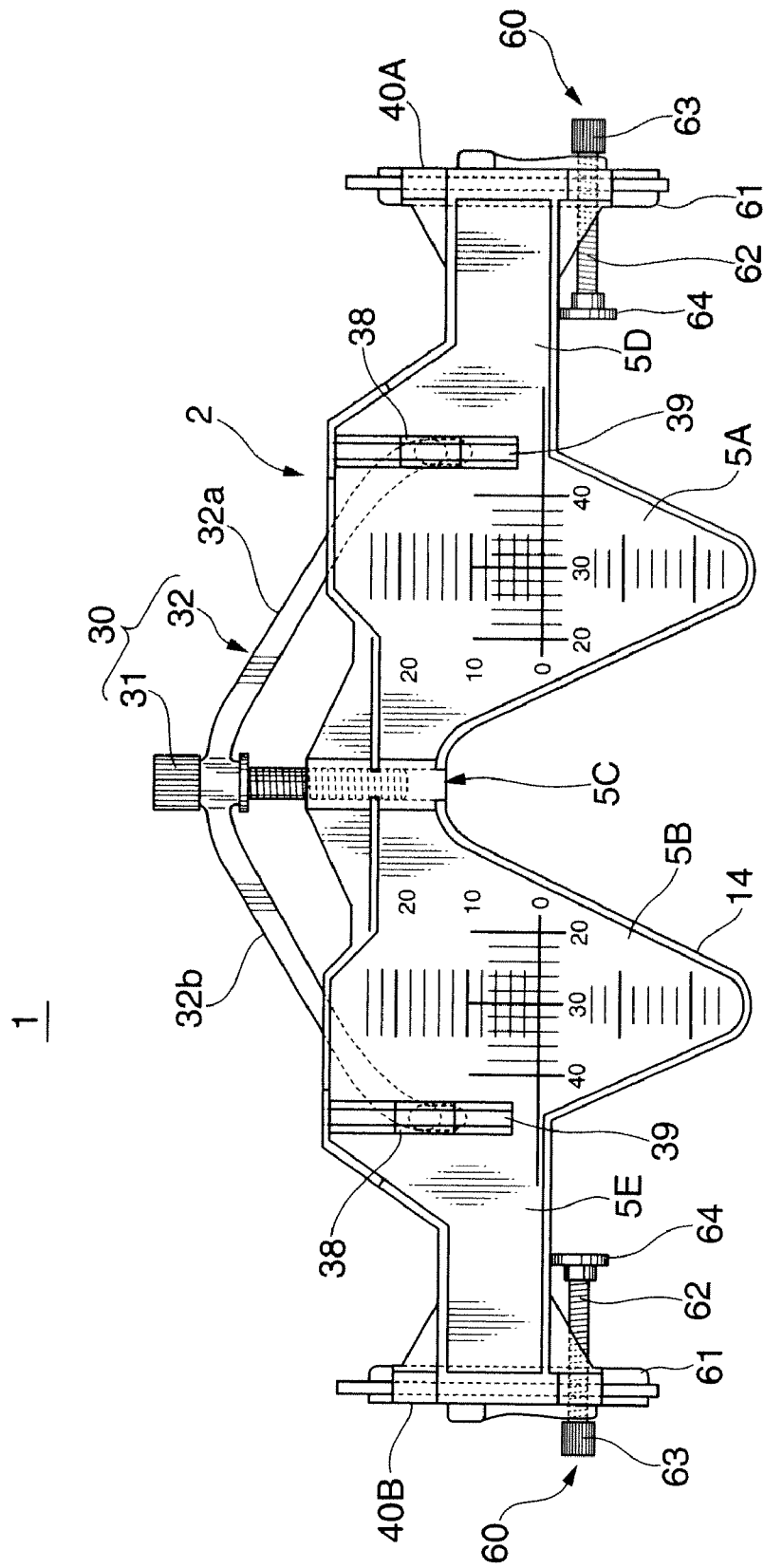
FIG. 2 is a front view of the spectacle measuring tool.

Referring to FIG. 1, the front plate 2 is formed from a plastic transparent plate with a thickness of about 1 to 1.5 mm, includes a reinforcing rib 4 integrally projecting from its peripheral edge, and has a length longer than the interval between left and right temples 3A and 3B of the spectacle frame 3. The front plate 2 also includes a left-eye counterpart 5A, a right-eye counterpart 5B, a connecting portion 5C, and a pair of left and right extending portions 5D and 5E. The left-eye counterpart 5A corresponds to a left-eye portion 3C of the spectacle frame 3. The right-eye counterpart 5B corresponds to a right-eye portion 3D of the spectacle frame 3. The connecting portion 5C connects the left-eye counterpart 5A and the right-eye counterpart 5B to each other. The extending portions 5D and 5E are integrally continuously formed in the outer portions of the left-eye counterpart 5A and right-eye counterpart 5B, respectively. The left-eye counterpart 5A and right-eye counterpart 5B are formed in bilaterally symmetrical, roughly inverted triangles about the connecting portion 5C. The left-eye counterpart 5A and right-eye counterpart 5B include horizontal lines 8 in the middle of their surfaces, an interpupillary distance measuring portion A (first measuring portion) which measures the interpupillary distance, and an fitting point height measuring portion B (second measuring portion) which measures the fitting point heights.

Figure 6:
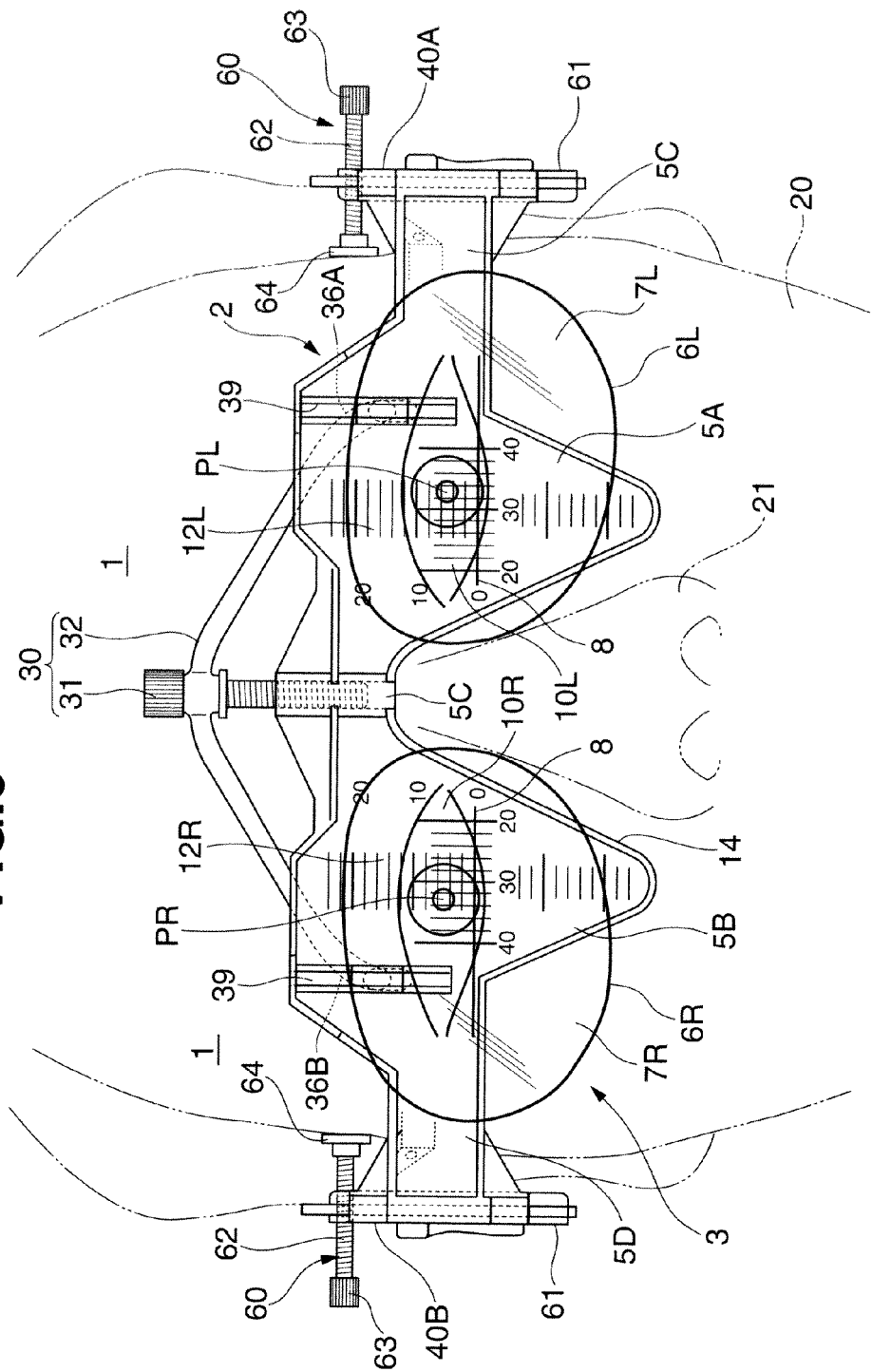
FIG. 6 is a front view showing the measurement state.

Referring to FIG. 6, the left-eye portion 3C of the spectacle frame 3 includes a left-eye frame rim 6L and a left-eye lens 7L fitted into it. Also, the right-eye portion 3D of the spectacle frame 3 includes a right-eye frame rim 6R and a right-eye lens 7R fitted into it. Note that when the frame rims 6L and 6R and lenses 7L and 7R are not distinguished between the left and right, they will be simply referred to as the frame rims 6 and the lenses 7, respectively, and their suffixes L (left) and R (right) will be omitted.

The horizontal lines 8 on the front plate 2 form PD horizontal reference lines (to be referred to as the PD horizontal reference lines 8 hereinafter) indicating a datum line DL (a virtual horizontal line connecting the geometric center points of the left and right frame rims 6L and 6R of the spectacle frame) of the frame rims 6 of the spectacle frame 3. "The geometric center points of the left and right frame rims 6L and 6R" mean points determined by the intermediate positions between the left and right edges of the lenses 7 attached to the frame rims 6L and 6R, and those between the upper and lower edges of the shapes of the lenses 7.

Referring to FIG. 1, the interpupillary distance measuring portion A of the front plate 2 measures the pupil center distance (FPD) while the subject keeps a straight gaze on a distant object. The interpupillary distance measuring portion A includes the PD horizontal reference lines 8, and a left-eye pupil horizontal position reading indicator scale 10L and right-eye pupil horizontal position reading indicator scale 10R for reading the positions, in the horizontal direction, of the pupils of the left and right eyes, respectively, with reference to the PD horizontal reference lines 8. The pupil horizontal position reading indicator scales 10L and 10R are graduated at an interval of 2 mm along the PD horizontal reference lines 8, and have numeric values 11 of 20, 30, and 40 (mm) indicating the distances from the center of the front plate 2 in the horizontal direction. The numeric values 11 are the half values of the geometric center distances of the left and right frame rims 6L and 6R, and indicate the monocular PD of the far interpupillary distance (FPD).

The fitting point height measuring portion B the front plate 2 measures the positions, in the height direction, of the pupils of the left and right eyes with reference to the PD horizontal reference lines 8, i.e., the datum line DL. The fitting point height measuring portion B includes a left-eye pupil height position reading indicator scale 12L and right-eye pupil height position reading indicator scale 12R. The pupil height position reading indicator scales 12L and 12R are graduated at an interval of 2 mm at positions above and below the PD horizontal reference lines 8 in the vertical direction, and have numeric values 13 of 10 and 20 (mm) indicating the distances from the PD horizontal reference lines 8. The indicator scales 12L and 12R are used to align the PD horizontal reference lines 8 with the datum line DL of the spectacle frame 3.

An inverted V-shaped recess 14 formed between the left-eye counterpart 5A and right-eye counterpart 5B of the front plate 2 is used to prevent a bridge of a nose 21 (FIG. 6) of a subject 20 from touching the lower edge of the front plate 2 when the spectacle measuring tool 1 is put on the subject 20 wearing the spectacle frame 3 in measurement. The recess 14 is positioned immediately beneath the connecting portion 5C.

The connecting portion 5C of the front plate 2 includes a cylindrical portion 24 which is open at its upper and lower ends, reinforcing ribs 25 connected to the cylindrical portion 24 on its two sides, and a metal nut 26 buried in the cylindrical portion 24. A height adjusting device 30 which adjusts the height of the front plate 2 relative to the spectacle frame 3 is attached to the connecting portion 5C.

The height adjusting device 30 is used to adjust the height of the front plate 2 so that the PD horizontal reference lines 8 on the front plate coincide with the datum line DL of the frame rims 6. The height adjusting device 30 includes a threaded body 31 which threadably engages with the metal nut 26 from above, and a height adjusting arm 32 to which the threaded body 31 is rotatably, unretractably attached. The height adjusting arm 32 is formed to extend in the horizontal direction, and includes a hole 35 (FIG. 5) which is formed at the center and rotatably, unretractably holds the threaded body 31. Left and right arm portions 32a and 32b obliquely extend to lower back sides so as to be positioned in the rear of the left-eye counterpart 5A and right-eye counterpart 5B of the front plate 2, and include mount portions 36A and 36B, respectively, formed at their distal ends. The mount portions 36A and 36B are mounted on the frame rims 6 of the spectacle frame 3 in measurement, and are bifurcated in inverted V shapes when viewed from the sides so as to have pairs of front and rear engaging sections 36a and 36b. Hence, inverted V-shaped recesses (FIG. 5) are formed in the lower surfaces of the pairs of engaging sections 36a and 36b so that the upper edges of the frame rims 6 of the spectacle frame 3 are inserted into the recesses 37. Rectangular connecting plates 38 are integrally formed at the distal ends of the engaging sections 36a positioned on the front sides of the pairs of front and rear engaging sections 36a and 36b. The connecting plates 38 are inserted into guide portions 39, formed in the left-eye counterpart 5A and right-eye counterpart 5B, respectively, of the front plate 2, from above to be relatively slidable to connect the front plate 2 and the height adjusting arm 32 to each other. Hence, even when one rotates the threaded body 31 with his or her hand, the height adjusting arm 32 does not rotate and the front plate 2 and threaded body 31 ascend/descend relative to each other. That is, assuming that the threaded body 31 (and the height adjusting arm 32) is fixed, the front plate 2 ascends/descends. Conversely, assuming that the front plate 2 is fixed, the threaded body 31 (and the height adjusting arm 32) ascends/descends. The guide portions 39 in the front plate 2 are formed from grooves which have T-shaped cross-sections and extend in the vertical direction, and are open in the upper surfaces of the left-eye counterpart 5A and right-eye counterpart 5B, respectively.

The extending portions 5D and 5E of the front plate 2 are formed from horizontally elongated rectangular plate portions, and include side plates 40A and 40B integrally continuously formed at their distal ends. The side plates 40A and 40B extend backward so as to form right angles with the front plate 2, thereby being opposed to each other, and have an interval between them, which is wider than that between the left and right temples 3A and 3B of the spectacle frame 3. Each of the side plates 40A and 40B is reinforced by a thick portion 41 and rib 42 so as to be prevented from sustaining damage, and includes, on its surface, a distance measuring portion C (a third measuring portion defined in claim 4) which measures the distance from the lens or the frame rim lateral surface to the corneal vertex. The left side plate 40A also includes, on its surface, a tilt angle measuring portion (a third measuring portion defined in claim 3) D which measures the tilt angle (pantoscopic angle) α (FIG. 7) of the lens 7.

The distance measuring portion C of each of the side plates 40A and 40B measures, e.g., a distance (a vertex distance S (see FIG. 7)) obtained by subtracting the lens thickness from the distance between the front vertices of the lens 7 and cornea, and the distance from the frame rim lateral surface to the corneal vertex. The distance measuring portion C includes a distance measurement indicator scale 45 which allows measurement from the lateral side of the subject 20. The distance measurement indicator scale 45 is graduated at an interval of 2 mm in the front-to-back direction of each of the side plates 40A and 40B, and has numeric values 46 of 0, 10, and 20 (mm) indicating the measurement distance.

Figure 4:
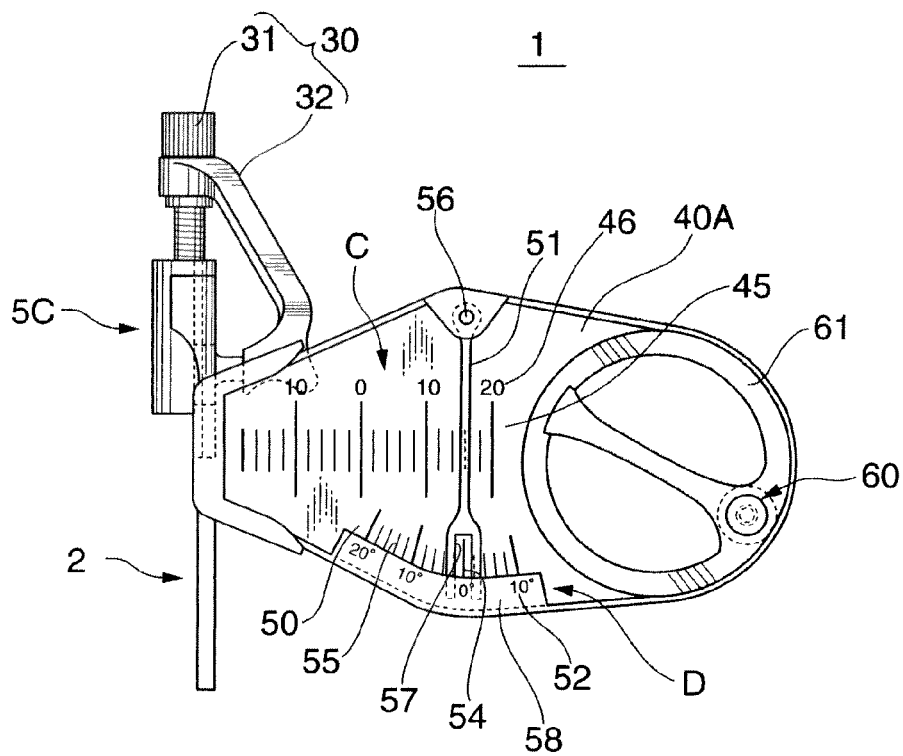
FIG. 4 is a left side view of the spectacle measuring tool.
Figure 5:
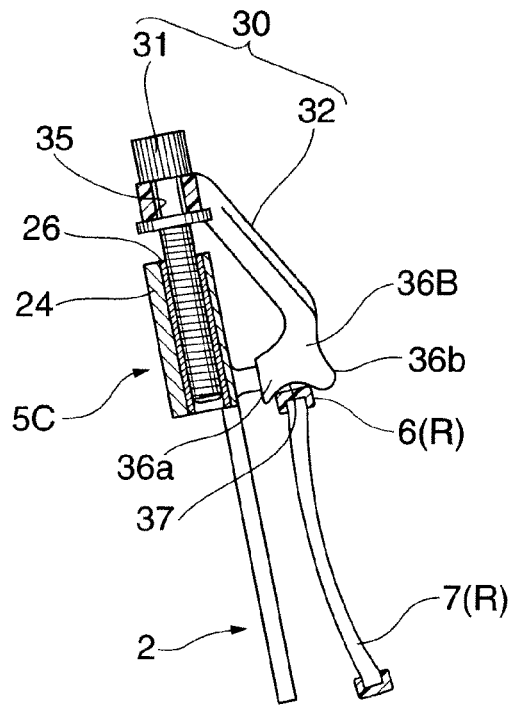
FIG. 5 is a sectional view taken along a line V-V in FIG. 1.

Referring to FIG. 4, the tilt angle measuring portion D measures the tilt angle α of the lens 7, and includes a tilt angle measurement indicator scale 50, a hand 51, and numeric values 52 of 0, 10, and 20(°) indicating the tilt angle of the lens 7. The tilt angle measurement indicator scale 50 includes a tilt angle measurement vertical reference line 54 and a plurality of angle indicator lines 55. The tilt angle measurement vertical reference line 54 is marked at the center of the lower portion on the surface of the side plate 40A in the front-to-back direction. The angle indicator lines 55 are marked at an interval equal to a tilt angle of 2° on both sides of the vertical reference line 54. The hand 51 is set at the center of the surface of the side plate 40A in correspondence with the tilt angle measurement indicator scale 50, has its upper end supported by a support shaft 56 to be pivotable in the front-to-back direction, points downward in the vertical direction while the subject 20 keeps a straight gaze on a distant object, and has an angle indicator line reading groove 57 which is formed at its lower end to extend in the vertical direction. While the spectacle measuring tool 1 is horizontally held, as shown in FIG. 4, the tilt angle measurement vertical reference line 54 is positioned at the center of the angle indicator line reading groove 57. The numeric values 52 indicating the tilt angle α of the lens 7 are marked on an indicator plate 58 (FIG. 3) integrally projecting from the lower portion of the surface of the side plate 40A in correspondence with the tilt angle measurement indicator scale 50. The indicator plate 58 is formed to be opposed to the surface of the side plate 40A with an appropriate spacing from it, so the lower end of the hand 51 is inserted in the gap between the indicator plate 58 and the side plate 40A.

The side plates 40A and 40B include pressing/adjusting devices 60 which are attached to their rear edges through rotary plates 61 and press against the side surface portions of the face (to be referred to as the face side portions hereinafter) of the subject 20. The pressing/adjusting device 60 includes a threaded rod 62, a handle 63 placed at the proximal end of the threaded rod 62, and a pressing portion 64 placed at the distal end of the threaded rod 62. The threaded rod 62 is externally screwed into a screw hole 65 formed in the rotary plate 61 near its outer periphery. The rotary plates 61 are used to adjust the positions of the pressing/adjusting devices 60 and, eventually, to adjust the entire spectacle measuring tool 1 in the vertical direction with reference to the central portions of the rotary plates 61 by fixing the pressing/adjusting devices 60 on the subject 20. The rotary plates 61 are rotatably fitted into attachment holes 66 formed in the side plates 40A and 40B on their rear edges so as to be prevented from slipping. Projections and recesses are formed in the outer peripheral surfaces of the rotary plates 61 and the inner peripheral surfaces of the attachment holes 66 to engage with each other, thereby moderating rotation of the rotary plates 61.

Measurement methods for the measuring portions A to D of the spectacle measuring tool 1 with the foregoing structure will be described next with reference to FIGS. 6 and 7.

In measurement, the spectacle measuring tool 1 is put on the subject 20 wearing the spectacle frame 3. More specifically, the left and right mount portions 36A and 36B of the height adjusting arm 32 are mounted on the left and right frame rims 6L and 6R of the spectacle frame 3, and the height adjusting device 30 adjusts the height of the front plate 2 relative to the spectacle frame 3 using the threaded body 31. That is, as the threaded body 31 rotates, the front plate 2 ascends/descends relative to the height adjusting arm 32 to align the PD horizontal reference lines 8 with the datum line DL of the frame rims 6. In this case, the left and right pupil height position reading indicator scales 12L and 12R read the datum line DL of the frame rims 6. More specifically, when it is visually observed which graduation lines on the upper and lower sides of zero graduations (PD horizontal reference lines 8) of the pupil height position reading indicator scales 12L and 12R coincide with the upper and lower edges of the frame rims 6, and the height of the spectacle measuring tool 1 is adjusted so that the scales 12L and 12R indicate identical graduation lines, the PD horizontal reference lines 8 coincide with the datum line DL. Fine vertical position adjustment as in this case can also be performed after the spectacle measuring tool 1 is put on the subject 20 wearing the spectacle frame 3.

After the height of the front plate 2 is adjusted, the tilt of the spectacle measuring tool 1 in the front-to-back direction is adjusted to make the front plate 2 and lenses 7 parallel to each other. The tilt of the spectacle measuring tool 1 is adjusted by visually observing the front plate 2 and lens 7 through the side plate 40A or 40B to confirm whether these two members are parallel to each other, and tilting the spectacle measuring tool 1 so that they become parallel to each other if they are not parallel to each other. After that, the handles 63 are turned while pressing the pressing portions 64 against the face side portions of the subject 20 by rotating the threaded rods 62 of the left and right pressing/adjusting devices 60 in the screwing direction to screw the threaded rods 62, thereby adjusting the side plates 40A and 40B to be parallel to the temples 3A and 3B of the spectacle frame 3. In this way, the spectacle measuring tool 1 is put on the subject 20 wearing the spectacle frame 3 and, and the mounting of the spectacle measuring tool 1 is completed.

In this mounting state, the interpupillary distance is measured by confirming the positions of left and right pupils PL and PR of the subject 20 through the front plate 2, and reading the distances from the middle of the bridge of the nose 21 to the centers of the two pupils using the left-eye pupil horizontal position reading indicator scale 10L and right-eye pupil horizontal position reading indicator scale 10R, respectively.

The fitting point heights from the PD horizontal reference lines 8 are measured by reading them using the left-eye pupil height position reading indicator scale 12L and right-eye pupil height position reading indicator scale 12R.

Figure 7:
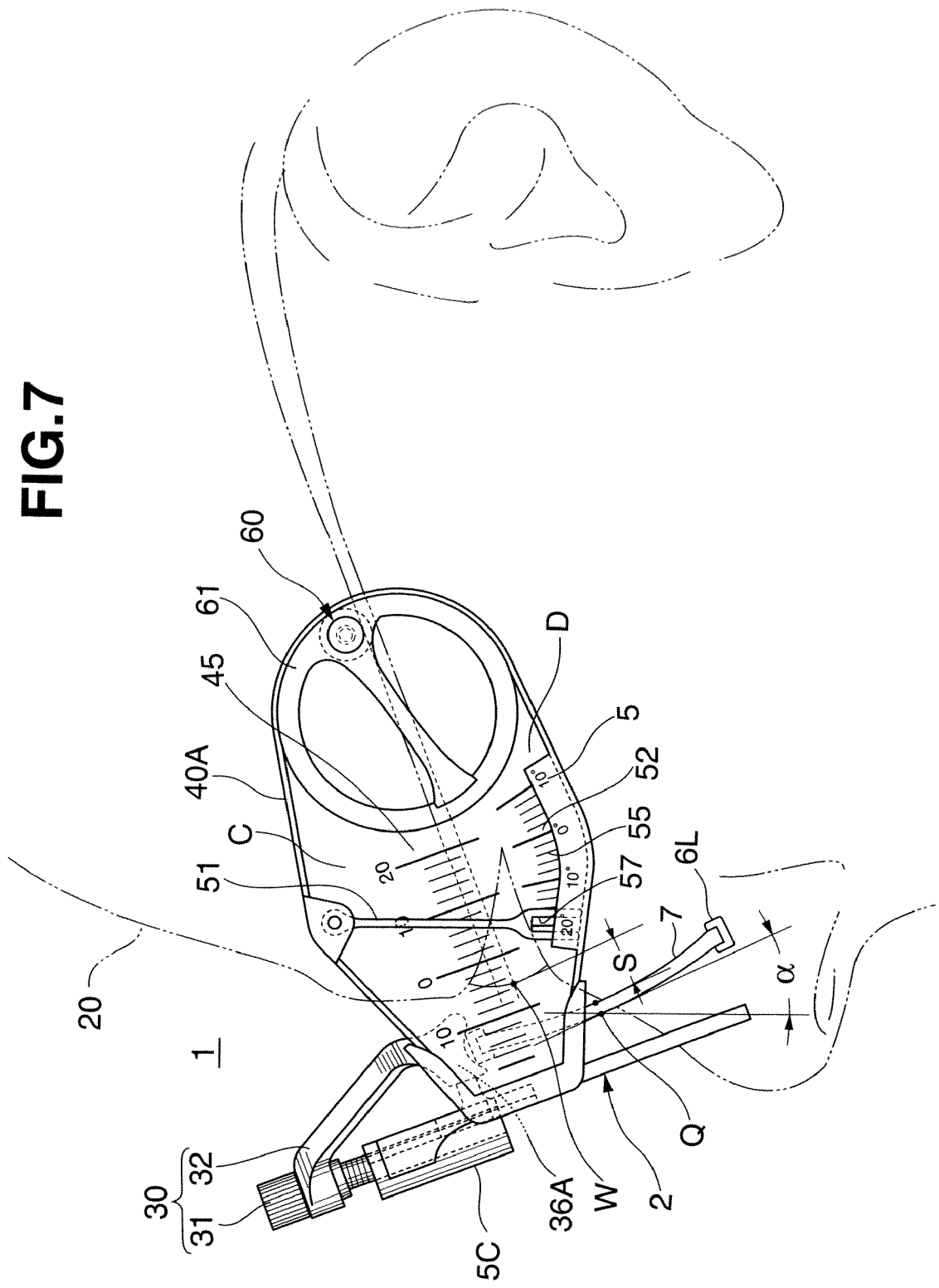
FIG. 7 is a left side view showing measurement state.

Referring to FIG. 7, the vertex distance S is measured by reading it using the distance measurement indicator scale 45 of the side plate 40A. That is, a corneal vertex W of the subject 20 and a front vertex Q of the lens 7 are visually measured, and their distance is read using the distance measurement indicator scale 45. At this time, the distance from zero to the corneal vertex W is read, that from zero to the front vertex Q is read, and their difference (Q−W) is calculated. A value obtained by subtracting the thickness of the lens 7 at the center from the calculated value is determined as the vertex distance S.

When the spectacle measuring tool 1 is used to customize spectacles for a subject, the distance between the corneal vertex W and the frame rim 6L or 6R is measured. In this case, the distance between the corneal vertex W and an arbitrary portion on the frame rim 6L or 6R is measured in the same way as the measurement of the vertex distance. An arbitrary portion on the frame rim 6L or 6R is used in that case because the portion to be measured differs depending on the thickness and shape of the frame rim 6. In case of a frame rim, formed from a nylon string, such as a nylon string frame, the distance from the nylon string to the corneal vertex W is measured using the distance measurement indicator scale 45.

The vertex distance S needs to be maintained at a distance designated upon prescription in advance. A distance from 12 mm to 15 mm is normally designated. If the vertex distance S is longer than the designated distance, the wearer feels weaker myopia and stronger hyperopia than he or she should really feel because the dioptric power of the lens 7 shifts to the plus side. In contrast, if the vertex distance S is shorter than the designated distance, the wearer feels stronger myopia and weaker hyperopia than he or she should really feel because the dioptric power of the lens 7 shifts to the minus side. It is therefore important to measure and confirm whether the vertex distances S of the left and right corneas are appropriately maintained at the same distances before and after the customization of spectacles.

Again referring to FIG. 7, the tilt angle $\alpha$ of the lens 7 is measured by reading the tilt of the hand 51 from the angle indicator lines 55 while the subject 20 faces front. That is, since the spectacle measuring tool 1 is maintained at the same angle as the spectacle frame 3, as shown in FIG. 7, it is visually observed which angle indicator line 55 falls within the angle indicator line reading groove 57 to read the tilt angle $\alpha$ of the lens 7. For example, the lens 7 has a tilt angle $\alpha$ of 20° in FIG. 7 because the 10th angle indicator line 55 toward the front side from the tilt angle measurement vertical reference line 54 falls within the angle indicator line reading groove 57.

The lens 7 is designated such that the aberration of its dioptric system is corrected with highest accuracy when the line of sight of the wearer coincides with the principal axis of the lens 7. On the other hand, when the wearer gazes into the distance, his or her line of sight tilts downward by 5° to 10° with respect to the horizontal line. Hence, spectacles for distance need to include frame rims 6 with a tilt angle of 5° to 10° so that the normal lines of sight coincide with the optical axes of the lenses. Spectacles for reading need to include frame rims 6 with a tilt angle of 12° to 15° assuming that the wearer keeps a downward gaze in front of him or her. Bifocal spectacles desirably include frame rims 6 with a tilt angle of 10° to 12°. It is important to measure and confirm whether the tilt angles are appropriately maintained before and after the customization of spectacles based on the foregoing standards.

In this manner, the spectacle measuring tool 1 according to the present invention includes the height adjusting device 30 which adjusts the height of the front plate 2. This facilitates precise alignment of the PD horizontal reference lines 8 marked on the front plate 2 with the datum line DL of the frame rims 6 when the spectacle measuring tool 1 is put on the subject 20 wearing the spectacle frame 3, and therefore makes it possible to precisely measure the interpupillary distance and the fitting point heights. Also, the mount portions 36A and 36B of the height adjusting arm 32 of the height adjusting device 30 are mounted on the frame rims 6 of the spectacle frame 3 so that the pair of left and right pressing/adjusting devices 60 press against the face side portions of the subject 20. This makes it possible to put the spectacle measuring tool 1 on the subject 20 in a stable state, and, in turn, makes it possible to adjust the temples 3A and 3B of the spectacle frame 3 and the side plates 40A and 40B to be parallel to each other. Hence, the spectacle measuring tool 1 can precisely measure the interpupillary distance and the fitting point heights without its movement and tilting during the measurement.

Although a tilt angle measuring portion D is placed only on the left side plate 40A in the above-described embodiment, the present invention is not limited to this. Alternatively, a tilt angle measuring portion D may be placed on the right side plate 40B, or tilt angle measuring portions D may be placed on both the side plates 40A and 40B. Similarly, a distance measuring portion C may be placed on one of the left and right side plates 40A and 40B. Further, if neither the distance from the lens or the frame rim lateral surface to the corneal vertex nor the tilt angle is measured, the spectacle measuring tool 1 may be dedicated to measurement of only the interpupillary distance and the fitting point heights.

Although an example in which the spectacle measuring tool 1 is applied to the spectacle frame 3 including the frame rims 6 has been given in the above-described embodiment, the spectacle measuring tool 1 is commonly used for spectacle frames such as a two-point frame and a nylon string frame.

As described above, in a preferred embodiment of the present invention, a height adjusting device includes a threaded body which threadably engages with a screw hole formed in a front plate at the center, and a height adjusting arm which is attached to the threaded body to extend in the horizontal direction. The height adjusting arm includes, at its left and right ends, mount portions mounted on a spectacle frame. The mount portions are connected to guide portions, formed in the front plate, to be relatively slidable in the vertical direction. Hence, as the threaded body rotates while the mount portions of the height adjusting arm are mounted on the spectacle frame, the front plate ascends/descends along the threaded body to adjust the height of the front plate relative to the spectacle frame.

Also, in the preferred embodiment of the present invention, at least one of a pair of left and right side plates includes a third measuring portion which measures the tilt angle of a lens. This third measuring portion can measure the tilt angle of a lens necessary for the measurer.

Also, in the preferred embodiment of the present invention, at least one of the pair of left and right side plates includes a fourth measuring portion which measures the distance from the lens or the frame rim lateral face to the corneal vertex. This fourth measuring portion can measure the vertex distance and the distance from, e.g., the frame rim top portion or rear portion when viewed from the side of the frame rim or a beveled groove to the corneal vertex.

Moreover, in the preferred embodiment of the present invention, the spectacle measuring tool includes rotary plates including the pair of left and right side plates attached to their rear edges, and pressing/adjusting devices are attached to the side plates through the rotary plates. Hence, when the pressing/adjusting devices have their heights adjusted by rotating the rotary plates, they can be prevented from pressing against the temples of the spectacle frame.

The invention claimed is:

1. A spectacle measuring tool comprising:
a transparent, front plate which comprises a first measuring portion which measures an interpupillary distance and a second measuring portion which measures fitting point heights, and is attached to a front portion of a spectacle frame;
a height adjusting device which adjusts a height of said front plate relative to the spectacle frame;
a pair of left and right side plates placed on two, left and right edges of said front plate to extend backward; and a pair of left and right pressing/adjusting devices which are attached to said respective side plates, press against face side portions of a subject, and adjust said side plates to be parallel to temples of the spectacle frame.

2. A spectacle measuring tool according to claim 1, wherein said height adjusting device comprises a threaded body which threadably engages with a screw hole formed in said front plate at the center, and a height adjusting arm which is attached to said threaded body to extend in a horizontal direction, said height adjusting arm includes, at two, left and right ends thereof, mount portions mounted on the spectacle frame, and said mount portions are connected to guide portions, formed in said front plate, to be relatively slidable in a vertical direction.

3. A spectacle measuring tool according to claim 1, wherein at least one of said pair of left and right side plates comprises a third measuring portion which measures a tilt angle of a lens.

4. A spectacle measuring tool according to claim 1, wherein at least one of said pair of left and right side plates comprises a third measuring portion which measures a distance from one of a lens and a frame rim lateral surface to a corneal vertex.

5. A spectacle measuring tool according to claim 1, wherein said pair of left and right plates further comprise rotary plates attached to rear edges thereof, and said pressing/adjusting devices are attached to said side plates through said rotary plates.

* * * * *

UNITED STATES PATENT AND TRADEMARK OFFICE
CERTIFICATE OF CORRECTION

PATENT NO. : 7,996,997 B2  
APPLICATION NO. : 12/809018  
DATED : August 16, 2011  
INVENTOR(S) : Hans Warntjes and Takashi Hatanaka Page 1 of 1

It is certified that error appears in the above-identified patent and that said Letters Patent is hereby corrected as shown below:

On the Title Page, in Item [56] under U.S. Patent Documents, at line 2, please delete "Padula net al." and insert --Padula II et al.--

Signed and Sealed this
Twenty-eighth Day of February, 2012

David J. Kappos
*Director of the United States Patent and Trademark Office*